United States Patent [19]

Croizy et al.

[11] Patent Number: 5,395,966
[45] Date of Patent: Mar. 7, 1995

[54] PROCESS FOR THE MANUFACTURE OF ACRYLOYL CHLORIDE

[75] Inventors: Jean-François Croizy, Farschviller; Paul Grosius, Petite Rosselle, both of France

[73] Assignee: Atochem, Paris, France

[21] Appl. No.: 277,298

[22] Filed: Jul. 22, 1994

Related U.S. Application Data

[63] Continuation of Ser. No. 51,791, Apr. 26, 1993, abandoned, which is a continuation of Ser. No. 795,272, Nov. 20, 1991, abandoned, which is a continuation of Ser. No. 598,671, Jan. 2, 1991, abandoned.

[30] Foreign Application Priority Data

Mar. 6, 1989 [FR] France .................. 89 02918

[51] Int. Cl.$^6$ ............................. C07C 69/62
[52] U.S. Cl. .................................. 562/861
[58] Field of Search .......................... 562/861

[56] References Cited

U.S. PATENT DOCUMENTS

| | | | |
|---|---|---|---|
| 1,921,761 | 8/1933 | Mills | 562/861 |
| 1,963,749 | 8/1933 | Kyrides | 562/861 |
| 3,691,217 | 9/1972 | McCann | |
| 4,623,491 | 11/1986 | Siegemund et al. | |

FOREIGN PATENT DOCUMENTS

| | | | |
|---|---|---|---|
| 758209 | 4/1971 | Belgium | 562/861 |
| 0082336 | 5/1982 | Japan | 562/861 |

*Primary Examiner*—Alan Siegel
*Attorney, Agent, or Firm*—Finnegan, Henderson, Farabow, Garrett & Dunner

[57] ABSTRACT

Acryloyl chloride is obtained by reaction of acrylic acid with phenylchloroform in the presence of at least one Lewis acid as catalyst and of at least one polymerization inhibitor. According to the invention the catalyst is chosen from zinc oxide and zirconium tetrachloride and the reaction is conducted at a temperature of at least 105° C. In a preferred embodiment acrylic acid is added to the mixture consisting of phenylchloroform, the catalyst and the polymerization inhibitor and heated to a temperature of at least 105° C., the acryloyl chloride formed distilling off as soon as the introduction of acrylic acid begins.

Acryloyl chloride is a highly reactive synthesis intermediate.

13 Claims, No Drawings

PROCESS FOR THE MANUFACTURE OF ACRYLOYL CHLORIDE

This application is a continuation of prior application Ser. No. 08/051,791, filed Apr. 26, 1993, now abandoned, which is a continuation of application Ser. No. 07/795,272, filed Nov. 20, 1991, abandoned, which is a continuation of application Ser. No. 07/598,671, filed Jan. 2, 1991, abandoned.

The present invention relates to a process for the manufacture of acryloyl chloride by reaction of acrylic acid with phenylchloroform.

Acryloyl chloride is a highly reactive synthesis intermediate. Access routes to this acid chloride, through the intermediacy of conventional reactants, such as phosgene, sulphonyl chloride, phosphorus tri- or pentachlorides, and the like, represent a complex technology, on account of the formation of HCl and of the reactivity of the acrylic double bond. This results in a significant drop in yield. However, another access route to acryloyl chloride is known, based on the reaction of acrylic acid with phenylchloroform in the presence of a Lewis acid as catalyst and of an inhibitor of acrylic acid polymerization, benzoyl chloride being also formed by the reaction. The reaction scheme for the latter, which consists of a solvolysis of phenylchloroform by acrylic acid, is the following:

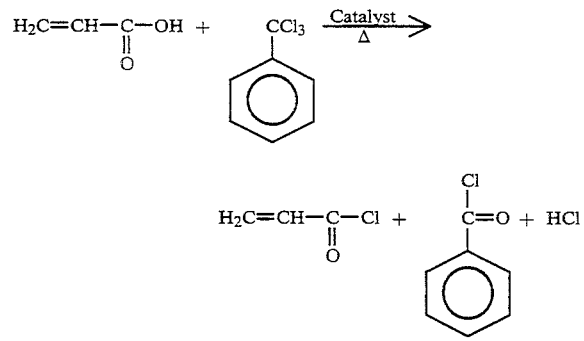

U.S. Pat. No. 3,691,217 describes, in its Example 19, the manufacture of acryloyl chloride by this method, the reaction being conducted at a temperature of 100° C. and the catalyst employed being stannic chloride.

Various by-products are capable of forming in the reaction of acrylic acid with phenylchloroform, by reaction between acrylic acid and an acid chloride (formation of anhydride and of HCl promoted by a temperature increase), by exchange reaction between benzoyl chloride and acrylic acid (formation of benzoic acid) and, above all, as shown below, addition of hydrochloric acid to the acrylic double bond. Kinetic data show, in fact, that acrylic acid reacts better with HCl than its associated chloride and that, whatever the reaction path followed, 3-chloroacryloyl chloride is obtained as the predominant by-product:

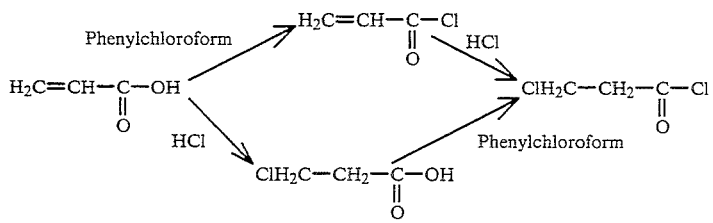

The abovementioned U.S. patent does indeed show this parallel production of 3-chloroacryloyl chloride, since in its Example 19 it is indicated that 20% by weight of 3-chloroacryloyl chloride is formed, a large quantity preventing the industrial exploitation of this process.

To solve this difficulty and to obtain an acryloyl chloride of high purity, in a good yield, applicants have found that this same reaction could be conducted at relatively high temperatures, contrary to the indications of the prior art, which recommends moderate temperatures when the reaction mixture contains acrylic acid, bearing in mind the low thermal stability of these acids with, furthermore, the use of catalysts other than SnCl$_4$.

The subject of the present invention is therefore a process for the manufacture of acryloyl chloride by reaction of acrylic acid with phenylchloroform in the presence of at least one Lewis acid as catalyst and of at least one polymerization inhibitor, characterized in that the catalyst is chosen from zinc oxide and zirconium tetrachloride and that the reaction is conducted at a temperature of at least 105° C.

The reaction is generally conducted with a substantially molar ratio of acrylic acid to phenylchloroform.

In a preferred embodiment acrylic acid is added to the mixture consisting of phenylchloroform, the catalyst and the polymerization inhibitor, and heated to a temperature of at least 105° C., the acryloyl chloride formed distilling off as soon as the introduction of acrylic acid begins.

Bearing in mind the high temperature level necessary according to the invention to obtain an acryloyl chloride of high quality, and bearing in mind the low boiling point of this product, it is indispensable to employ very efficient refrigeration, necessary all the more since this product is lachrymogenic.

The addition of acrylic acid is preferably carried out via the bottom of the reactor, to avoid a loss of reactant by entrainment with HCl, to favour the reaction of acrylic acid with phenylchloroform and to limit the addition of HCl to the acrylic double bond as a result of a lower HCl concentration. The acryloyl chloride formed is recovered at the outlet of a distillation column mounted on the reactor outlet, in the upper part of the latter. The acrylic acid is introduced at a rate which depends on the apparatus employed and the ease of removing the hydrochloric acid formed and of condensing the volatile acryloyl chloride.

The reaction is preferably conducted according to the invention at a temperature of between 105° C. and 180° C. In particular, the chosen temperature is maintained throughout the addition of the acrylic acid, and is then progressively raised to enable the distillation of acryloyl chloride to be completed. Once this distillation is completed, the remaining benzoyl chloride is collected by distillation, preferably under reduced pressure. The reaction of acrylic acid with phenylchloroform, for its part, is generally conducted at atmospheric pressure; it could, however, be performed at a pressure below atmospheric pressure.

The length of the reaction according to the invention depends on the quantity of catalyst and on the rate of introduction of acrylic acid. It is especially between 0.5 and 5 hours.

Furthermore, the quantity of catalyst and the quantity of polymerization inhibitor usually employed, lie between approximately 0.1 and 5% by weight and approximately 0.05 to 2% by weight respectively, relative to the quantity of acrylic acid introduced.

Hydroquinone, hydroquinone methyl ether, ditertbutyl-para-cresol, phenothiazine and copper chloride are examples of polymerization inhibitors which can be employed in accordance with the invention. Furthermore, the fact that the reaction of the invention is conducted in the presence of air already provides an inhibition of the polymerization of acrylic acid.

The following examples are intended to illustrate the present invention better without, however, limiting its scope. In these examples the percentages are expressed by weight. Example 5 is a comparative example.

EXAMPLES 1 to 5

General Operating Procedure

The parameters which vary from one example to another and the results obtained appear in the Table below.

Into a reactor of 1-liter capacity, jacketed and equipped with a central mechanical stirring device, an adiabatic column (approximately 15 theoretical plates) and highly efficient reflux condensers there are introduced 0.14 g of hydroquinone (0.1% by weight relative to the acrylic acid to be introduced), a given quantity of zinc oxide or zirconium tetrachloride as catalyst and 399.2 g of phenylchloroform (2 moles; purity: 97.9%).

The whole is heated to the temperature shown. When this temperature is reached, 144 g of glacial acrylic acid (2 moles) are added at the bottom of the reactor, over a period of approximately 70 minutes, by means of a metering pump.

The temperature shown is maintained throughout the addition of the acrylic acid. Acryloyl chloride distills off simultaneously at atmospheric pressure (temperature at the head of the column: approximately 51° C.). Then, after the addition of acrylic acid has been completed, the temperature is progressively raised to approximately 180° C. to permit a complete distillation of acryloyl chloride. Hydrochloric acid, which is formed simultaneously during the reaction is trapped by bubbling into water.

At the end of the reaction the benzoyl chloride formed is distilled off under reduced pressure (temperature at the head of the column: approximately 100° C.; pressure: $6.7 \times 10^3$ Pa).

TABLE

| Example | Catalyst | Temperature °C. | Acryloyl chloride (moles**) | 3-Chloroacryloyl chloride (moles**) |
|---|---|---|---|---|
| 1 | ZnO 0.72 g | 110 | 0.74 | 0.01 |
| 2 | ZnO 0.72 g | 162 | 0.74 | 0.005 |
| 3 | ZrCl$_4$ 0.72 g | 120 | 0.78 | 0.005 |
| 4 | ZrCl$_4$ 2.06 g | 120 | 0.78 | 0.005 |
| 5* (comp.) | ZnO 0.72 g | 92 | 0.61 | 0.36 |

*The reaction took 1 h and was conducted in two stages : the reaction proper and the distillation of the products formed.
**Per mole of acrylic acid introduced.

We claim:

1. A process for the manufacture of acryloyl chloride comprising the step of:
   reacting acrylic acid with phenylchloroform in a reaction zone in the presence of at least one Lewis acid catalyst selected from zinc oxide and zirconium tetrachloride and of at least one polymerization inhibitor at a temperature of between 110° C. and 180° C., said acryloyl chloride when formed being substantially free of a 3-chloroacryloyl chloride by-product.

2. The process according to claim 1, wherein the acrylic acid is added to a mixture containing the phenylchloroform, the catalyst and the polymerization inhibitor, and the mixture is heated to said temperature of between 110° C. and 180° C. whereby acryloyl chloride formed is distilled off when the introduction of acrylic acid begins.

3. The process according to claim 2, wherein the acrylic acid is added at the bottom of the reaction zone and the acryloyl chloride formed is recovered from an outlet of a distillation column in the upper part of the reaction zone.

4. The process according to claim 3, wherein the reaction temperature is maintained throughout the addition of the acrylic acid, and then raised progressively to complete distillation of acryloyl chloride.

5. The process according to claim 2, wherein the reaction temperature is maintained throughout the addition of the acrylic acid, and then raised progressively to complete distillation of acryloyl chloride.

6. The process according to claim 3, wherein the reaction is carried out at atmospheric-pressure.

7. The process according to claim 1, wherein the reaction is carried out at atmospheric pressure.

8. The process according to claim 3, wherein the acrylic acid and phenylchloroform are present in a substantially molar ratio.

9. The process according to claim 1, wherein the acrylic acid and phenylchloroform are present in a substantially molar ratio.

10. The process according to claim 3, wherein the catalyst is employed in an amount between 0.1 and 5% by weight relative to the quantity of acrylic acid.

11. The process according to claim 1, wherein the catalyst is employed in an amount between 0.1 and 5% by weight relative to the quantity of acrylic acid.

12. The process according to claim 3, wherein the polymerization inhibitor is selected from hydroquinone, hydroquinone methyl ether, di-tert-butyl-para-cresol, phenothiazine and copper chloride and employed in a proportion of 0.05 to 2% by weight relative to the quantity of acrylic acid.

13. The process according to claim 1, wherein the polymerization inhibitor is selected from hydroquinone, hydroquinone methyl ether, di-tert-butyl-para-cresol, phenothiazine and copper chloride and employed in a proportion of 0.05 to 2% by weight relative to the quantity of acrylic acid.

* * * * *

UNITED STATES PATENT AND TRADEMARK OFFICE
CERTIFICATE OF CORRECTION

PATENT NO. : 5,395,966
DATED : March 7, 1995
INVENTOR(S) : Jean-Francois Croizy and Paul Grosius It is certified that error appears in the above-identified patent and that said Letters Patent is hereby corrected as shown below:

Claim 6, col. 4, line 43, "atmospheric-pressure" should read --atmospheric pressure--.

Signed and Sealed this

Second Day of May, 1995

Attest:

BRUCE LEHMAN

Attesting Officer    Commissioner of Patents and Trademarks